United States Patent [19]
Wang

[11] Patent Number: 5,783,667
[45] Date of Patent: Jul. 21, 1998

[54] APOPTOSIS SPECIFIC TP30 PROTEIN

[75] Inventor: Eugenia Wang, Montreal, Canada

[73] Assignee: Sir Mortimer B. Davis-Jewish General Hospital, Montreal, Canada

[21] Appl. No.: 362,221

[22] Filed: Dec. 23, 1994

[51] Int. Cl.$^6$ .............................. C07K 1/00; C12P 21/08; A61K 39/00; A61K 39/395

[52] U.S. Cl. .................. 530/350; 424/184.1; 424/130.1; 530/387.3

[58] Field of Search ...................... 435/6, 69.1; 530/350, 530/387.3; 424/130.1, 184.1

[56] References Cited

PUBLICATIONS

Schipper et al; *Expression of terminin, a sequence-related cytoplasmic protein, in the aging rat brain*; Brain Research; vol. 635; pp. 224–230; 1994.

Wang et al; *Granula Presence of Terminin is the Marker to Distinguish Between the Senescent and Quiescent States*; Journal of Cellular Physiology; vol. 147; pp. 514–522; 1991.

Mitmaker et al; *Temporal realationships of statin and terminin expression in ventral lobe of rat prostate prostate following castration*; European Journal of Histochemistry; vol. 37; pp. 295–301; 1993.

Wang et al; *Control of Fibroblase Senescence and Activation of Programmes Cell Death*; Journal of Cellular Biochemistry; vol. 54; pp. 432–439; 1994.

Yang et al; *Expression of terminin in the rat brain during neuronal differenttiation*; Brain Research; vol. 615; pp. 71–79; 1993.

Yang et al; *Terminin (Tp 63/60), a novel cell senescence-related protein, is present in the aging human hippocampus*; Brain Research; vol. 644; pp. 188–196; 1994.

Hebert et al; *Commitment to Cell Death is Signaled by the Appearence of Terminin Protein of 30 kDa*; Experimental Cell Research; vol. 210; pp. 10–18; 1994.

Primary Examiner—Ponnathapura Achutamurthy
Assistant Examiner—Hankyel T. Park
Attorney, Agent, or Firm—Iver P. Cooper

[57] ABSTRACT

Apoptosis or programmed cell death is a tightly regulated mechanism used by the body to eliminate excess cells in a given tissue. If this mechanism fails, resulting in too many cells, cancer may develop in certain tissues. If the mechanism is overactive, resulting in the destruction of too many cells, tissue degeneration can occur. Therefore being able to identify which cells are destined to undergo apoptosis is critical in allowing clinicians, pathologists and researchers to develop means to detect, diagnose or treat disorders wherein the natural regulation of cell death events is interrupted. The present inventor has identified a 30 kDa protein, designated Tp30, that is specific for cells that are programmed to die. A monoclonal antibody specific for Tp30 has also been identified. The Tp30 protein and monoclonal antibodies thereto are useful in the detection and therapy of disorders wherein the natural regulation of cell death events is interrupted. Such disorders include cancer, bone degeneration, autoimmune diseases, neurodegenerative diseases, cardiovascular disorder, ischemia, HIV-associated illness and kidney malfunction.

9 Claims, 7 Drawing Sheets

APOPTOSIS SPECIFIC TP30 PROTEIN

FIELD OF THE INVENTION

The present invention relates to a 30 kDa protein termed Tp30, that is specific for cells that are programmed to die. The present invention also relates to the use of monoclonal antibodies specific for Tp30. The Tp30 protein and monoclonal antibodies thereto are useful in the detection and therapy of disorders wherein the natural regulation of cell death events is interrupted. Such disorders include cancer, bone degeneration, autoimmune diseases, neurodegenerative diseases, cardiovascular disorder, ischemia, HIV-associated illness and kidney malfunction.

BACKGROUND OF THE INVENTION

Cells, the basic unit of every organism, usually follow a precise program of life span in every tissue. Starting from the very beginning, each cell in an embryo is destined for a particular tissue. During development, each cell reproduces itself and multiplies in number, thus producing the mass needed for the creation of the tissue. However, during this process of multiplication, more cells may be produced than are needed. Consequently, nature has provided a suicidal process to eliminate these extra cells. This process, termed programmed cell death or apoptosis, involves the activation of unique genes whose functions are involved in the actual killing process of the cells themselves. However, there are also genes which can counteract these "killer" genes and protect those cells that are meant to live. The genes that are involved in the killing action are termed death genes, and those that are involved in survival are termed anti-death genes.

During adulthood, the programmed cell death process is tightly controlled for each tissue. For some tissues, in general those tissues composed of cells that are permanently growth-arrested, i.e. their cell mass cannot be replenished by further cell replication, programmed cell death must not occur. If it does, the cells that die are a permanent loss to the system. This is the case for cardiomyocytes, neuronal and muscle cells as loss of these cells results in functional degeneration and eventual failure of tissue functions in brain, heart or muscle. In contrast, if cellular units such as epithelial cells in the breast or uterus of postmenopausal women are no longer needed, there is an active program of tissue regression to get rid of these cells. If and when the programmed cell death involved in this regression is derailed, extra cell mass will accumulate, which in turn can lead to the formation of cancer. Similarly, in the haemopoietic cell system, the balance between those cells living and those cells scheduled to die must be precisely regulated in order to provide a healthy cell mass. Tilting the balance in favor of more living than dying cells results in hyperplasia, a beginning point leading to neoplasia and subsequent cancer development.

The health status of any given tissue is dependent upon the number of cells that are living and functional. Too many cells, resulting from failure of programmed cell death, may result in cancer development in some tissues. On the other hand, too few cells, resulting from overactive programmed cell death, may result in degeneration in tissue such as brain, muscle and heart. Therefore, the method of marking out the death events, in terms of frequency, number and rate of cells that are designated to die, is most critical in allowing clinicians, pathologists and researchers informative means of detection, diagnosis and treatment.

Several genes have been identified as related to programmed cell death. These genes may be separated into two categories: those of known class and those of novel class. Included in the known class are the oncogenes and anti-oncogenes, such as c-myc, c-ras, E1A and p53, and several growth factors and cytokines. Included in the novel class are ced3, ced4, ced9, interleukin converting enzyme (ICE), reaper, and members of the bcl2 family. The applicability of the known gene class will be less specific, and in particular confusing, as to oncogene usage, one must clarify whether the application is related to cell growth or cell death.

In the case of the novel class, ced3, ced4, ced9 and reaper are found only in lower organisms such as *C. elegans*, a needle worm and fruitfly, and are not found in man. bcl2 and its related genes are useful only to study cells that survive, since this gene functions as a survival factor to protect cells from dying. ICE is a mammalian analogue of ced3. Therefore, marking specific dying cell populations can only be performed at present in mammalian cells by ICE. So far, large quantities of high-quality antibodies to ICE are not available. In addition, information on ICE's presence in normal and diseased tissues is also absent. Consequently, there is a real need for the identification of a protein marker that is specific for cells programmed to die. Such a marker can be used as a tool to detect or treat diseases wherein the natural regulation of cell death events is interrupted.

SUMMARY OF THE INVENTION

The present invention relates to the identification of a 30 kDa protein, termed Tp30, that is specific for cells that are programmed to die. The Tp30 protein is a proteolytic product of terminin. Terminin is a 90 kDa cytoplasmic protein that is expressed in permanently growth arrested and terminally differentiated cells and can be used to distinguish between temporarily and permanently growth arrested cells. Terminin was identified by preparing a monoclonal antibody (Mab 1.2) that identifies senescence specific but not quiescence dependent antigens. When Mab 1.2 was identified it was found to recognize terminin Tp90 in growing and quiescent cells and a 60 Kd protein Tp60 in senescent cells. Tp60 is the proteolytic product of posttranslational modification of the Tp90 protein. Tp60 is the marker distinguishing between senescence and quiescence.

Recently it was determined that Mab 1.2 also recognizes a 30 kDa protein (called terminin protein 30 or Tp30) in cells that are programmed to die. Tp30 (like Tp60) is a proteolytic product of Tp90. Therefore, not only can the presence of Tp30 be used as a marker for cell death commitment but also the ratio between Tp90 and Tp30 can be used as a quantitative index to denote the scope and frequency of programmed cell death in a given tissue.

The present invention thus provides the use of the Tp30 protein, the nucleic acid sequence coding for it and the monoclonal antibody that recognizes Tp30 (Mab 1.2) in the detection, or diagnosis or therapy of disorders where the natural regulation of cell death events is interrupted. In particular Tp30, nucleic acid sequences coding for it and Mab 1.2 can be used in the detection, diagnosis and therapy of cancer, bone degeneration, autoimmune diseases, neurodegenerative diseases, cardiovascular disorders, ischemia, HIV-associated illness, kidney malfunction, as well as other disorders where natural regulation of cell death events is interrupted. In particular, monoclonal antibodies to terminin protein Tp30 and terminin-like proteins may be used to define the pool size of dying cells in any given tissue. The invention also includes the use of nucleotide sequences coding for terminin and related genes, to detect the RNA such as mRNA and protein derived therefrom. Therefore, the monoclonal antibodies to terminin protein Tp30 and its related proteins, as well as the nucleotide sequences, can be used in a kit form for diagnostic purposes as well as assessment, in terms of scope and frequency of cell death in any biopsy tissues from either normal or disease conditions. These assessments of cell death incidents are necessary to determine disease staging, treatment regimen and the efficiency of either chemotherapeutic drug development or gene therapy. In addition, the monoclonal antibodies and nucleotide sequence to terminin, Tp30, and its related proteins can be used in a kit with a group of nonproliferation-specific markers such as statin, as a complete assessment of cell growth and survival status in any given tissues in terms of the size of the subpopulations of cells in growing (statin negative), nongrowing (statin positive), and dying (Tp30 positive) states.

The present invention can be carried out using various techniques known in the art. One example is the application of immunohistochemical studies with monoclonal antibodies to terminin protein Tp30 and its related proteins, on either biopsy or autopsy tissues. Another example is the application of labelling dying cells which are at different phases of the cell cycle in fluorocytometric studies. A third example is the application of immunoblotting techniques to examine the presence of Tp30 bands in the cell extracts of those tissues shown by immunohistochemical technique to be positive for the monoclonal antibody (Mab 1.2) to Tp30. A fourth example is the application of sequence-specific nucleotide probes to terminin protein, Tp30, to detect abnormality or normality of terminin protein Tp30 and its related genes in tissues of interest. Another example is the use of both monoclonal antibodies and nucleotide sequences to terminin protein, Tp30 as a kit to study the effectiveness of therapeutic treatment of drugs as well as various gene therapy protocols in both in vitro cultures and in vivo studies, for drug development and treatment efficacy evaluation. Included in this last example is also the future application of gene therapy protocols in the attempt to correct the disease situations where unscheduled incidents of programmed cell death occur.

In summary, the present invention provides a cost-effective and easy procedure that can be widely used in the evaluation of cell death frequency, and therefore the health status of any tissue, and can be routinely performed in any clinical laboratory.

DESCRIPTION OF THE DRAWINGS

FIG. 1. Effect of serum deprivation on DNA synthesis, survival, and terminin expression in mouse 3T3 fibroblasts. (A) Cell survival was measured for mouse 3T3 cells during serum deprivation. Cell viability was measured as described under Experimental Procedures using the trypan blue exclusion test. The data presented is the average of three experiments (± standard error of mean). Cell survival of the mouse 3T3 cells significantly decreases after 15 and 18 h of serum deprivation. (B.C) Detergent-insoluble fractions were prepared from proliferating sparse (SPA) and serum deprived (DEPRIVED) cells for the indicated times. One hundred fifty micrograms of proteins was loaded per lane. Control with PAI ascites which bears no specific antigenic reaction against cell extract of the same preparation is shown in the first lane. All the other lanes were incubated with the anti-terminin mouse monoclonal antibody (Mab 1.2). The synchronized fibroblasts were deprived of serum for 0.5, 6, 12, 24, 48, and 96 h. Electrophoresis and immunoblots with the PAI ascites and the Mab 1.2 antibody were performed as described under Experimental Procedures. Identifications of terminin proteins (as identified by their molecular weights) are shown on both sides. The Tp30 protein appears with serum deprivation as opposed to the presence of TP90/63/60 in sparse 3T3 fibroblasts.

FIG. 2. Study of expression of terminin in GM3529 fibroblasts during serum deprivation. Detergent-insoluble fractions were prepared from senescent GM3529 human diploid fibroblasts (HDF) under 10% serum (+serum) or serum-deprived (−serum) conditions for 28 days and immunoblotted with the anti-terminin mouse monoclonal antibody (Mab 1.2). Control with PAI ascites (PAI; of no specific activity) against a protein extract of HDF in 10% serum is shown in the first lane. Electrophoresis and immunoblots proceeded as previously described in the legend to FIG. 1. The band at 40 kDa (*) observed on the immunoblot with Mab 1.2 from the senescent culture is also observed in the PAI control lane against the same extract and is thus nonspecific. The presence of Tp30 is observed during serum deprivation in a protein extract from senescent human diploid fibroblasts and not in the same cell culture in the presence of serum.

FIG. 3. Study of the induction of Tp30 during cell death. A detergent-insoluble fraction was prepared from mouse 3T3 cells treated with 10 µM cytosine β-D-arabinofuranoside (Ara-C) for 24 h and immunoblotted with the anti-terminin mouse monoclonal antibody (Mab 1.2). Control with PAI ascites (PAI) against the same extract is included in the first lane. Electrophoresis and immunoblot analysis was pursued as previously described in the legend to FIG. 1. The appearance of Tp30 with cell death as induced by Ara-C in Swiss 3T3 cells is observed.

FIG. 4. Results of revival experiments and terminin expression in mouse 3T3 cells. Cells were deprived of serum for 1.5 to 96 h. All cultures were subsequently supplemented with fresh serum to a final concentration of 10% for 48 h (revival), as described under Experimental Procedures. Immunoblot analysis (as described in the legend to FIG. 1) was carried out against a protein extract obtained from cells that were serum deprived for 12 h and subsequently "revived" with medium supplemented with 10% serum for 48 h. Note the increased expression of Tp60.

FIG. 5. Inhibition of cell death by cycloheximide in Swiss 3T3 cells after serum deprivation. The Swiss 3T3 cells were synchronized by confluency for 24–48 h. (A) The fibroblasts were passaged to serum-free conditions without (open diamond) or with pretreatment for 30 min with cycloheximide at $10^{-3}$M (closed diamond), $10^{-4}$M (open square, dotted line), $10^{-5}$M (open square), $10^{-6}$M (closed square). Each data point is the average of triplicate culture wells. (B) The 3T3 cells were grown in confluency and then transferred to serum-deprived conditions (5 min) (lane A) or the fibroblasts were pretreated with $10^{-5}$M cycloheximide for 30 min and serum deprived for 24 h (lane B). Cell viability and immunoblot analysis were performed as described under Experimental Procedures. Cycloheximide pretreatment ($10^{-4}$M) can delay death induced by serum deprivation up to 24 h of the latter treatment and decrease the amount of Tp30 in these cells.

FIG. 6. Fluorescence micrographs showing terminin staining activity in mouse 3T3 cells during serum deprivation-induced cell death. The Swiss 3T3 cells were grown in 10% serum (A) and transferred to serum-free medium for 6 h (B), 24 h (C), or 96 h (D). Illustrations show immunofluorescence results. n. nucleus; c. cytoplasm. Magnification factor, ×480. Cells were stained as described under Experimental Procedures. Upon serum deprivation, diffuse immunostaining by the anti-terminin monoclonal antibody in the cytoplasm of the 3T3 cells, which becomes granular by 96 h of serum removal, was detected.

FIG. 7. Kinetics of the onset of apoptosis in mouse 3T3 fibroblasts. Mouse 3T3 cells were deprived of serum for 30 min. 2, 6, 12, 18, 24, and 48 h. Control cultures (0 h) included here are those of sparse cells density without serum deprivation. Twenty micrograms of DNA was loaded in each lane and analyzed as described under Experimental Procedures. DNA fragmentation to an oligonucleosomal ladder (apoptosis) became visible by 18 h of serum deprivation in 3T3 cells and increase in intensity with time.

DETAILED DESCRIPTION OF THE INVENTION

A. IDENTIFICATION OF TP30

In earlier studies the inventor determined that there was a biochemical difference in the terminin sub-species between young growing/nongrowing (terminin in the 90 kDa form) and senescent (terminin in the 60 kDa form) fibroblasts. The inventor observed that senescent fibroblasts were resistant to apoptosis upon serum deprivation up to 4 weeks and before this time there was no change in the molecular weight of terminin (Tp60). These results prompted the investigation of the modulation of terminin upon cell death induction.

The inventor studied changes in the size of terminin protein during apoptosis and concluded that the modification of terminin is one of the biochemical events in the pathways leading to an apoptotic death. In particular, they found that during apoptosis induced by serum deprivation in Swiss 3T3 mouse fibroblasts there is specific proteolytic degradating Tp90 and Tp60 into Tp30, a 30-kDa terminin polypeptide and this precedes the massive DNA fragmentation event. These findings suggest that the proteolytic product, present in the 30-kDa form (Tp30), can be used as a biochemical marker for signalling the "apoptotic-related" events in fibroblasts.

EXPERIMENTAL PROCEDURES

Cell lines and culture conditions. Mouse swiss 3T3 fibroblasts were cultured in Dulbecco's modified medium (DMEM) supplemented with glutamine, 10% fetal bovine serum (FBS), and 50 U/ml penicillin/50 µg/ml streptomycin. In each experiment $5 \times 10^5$ cells were seeded in 100-mm petri dishes. Normal human fibroblasts derived from a 66-year-old donor (GM 3529) were cultured to senescent state by a rigid schedule of serial passaging in the monolayer cultures as described in Wang, E and Tomaszewski, G. 1991. J.Cell. Physiol. 147:514. Exponentially growing 3T3 cells were cultured for 16 to 24 h in DMEM containing 10% FBS.

Serum deprivation and revival culturing conditions. For serum deprivation, the cells were grown to confluency ($3 \times 10^4$ cells/cm$^2$) in DMEM supplemented with 10% FBS and left in the quiescent state for 24–48 h. The cells were subsequently washed once with fresh DMEM, transferred to DMEM without serum at a lower cell density ($1.5 \times 10^4$ cells/cm$^2$), and incubated for up to 96 h. For the experiments to test the kinetics of revival ability of cells which had been deprived of serum for various time periods, the medium lacking nutrients was replaced with DMEM supplemented with 10% serum and the cells were left in the presence of serum-containing medium for 48 h.

Cell viability assay. Since dead cells detach from their substratum, we harvested the medium containing floating cells and collected the adhering cells by trypsin treatment. The two fractions were pooled and centrifuged at 1200 g for 10 min at 4° C. Cell viability of the total cell population was estimated by adding an equivalent volume of a 0.4% trypan blue solution (GIBCO Laboratories, Grand Island, N.Y.) to an aliquot of resuspended cells and incubating for 5 min. Stained and unstained cells were counted in an hemacytometer. Mean values obtained represent data of triplicates from each separate experiment. Statistical analysis for this assay and all other experiments in this paper was done using a two-tailed Mann-Whitney test.

Cycloheximide treatment. The mouse 3T3 fibroblasts were synchronized by culturing them to confluency and maintaining them in this state for 24 to 48 h. Cells were then treated with cycloheximide at concentrations of $10^{-3}$, $10^{-4}$, $10^{-5}$, and $10^{-6}$ M for 30 min and subsequently washed with fresh DMEM and transferred to serum-deprived conditions as described above.

DNA fragmentation. The technique was adapted from that described by Blin and Stafford in Nucleic Acids Res 3:2303–2308 (1976). Mouse 3T3 fibroblasts were washed in phosphate-buffered saline (PBS) and lysed in 10 mM Tris-HCl, 0.1 M EDTA, RNAse A (20 µg/ml), 0.5% SDS at pH 8.0 for 1 h. The suspension was further incubated for 3 h in the presence of proteinase K (Boehringer Mannheim, Laval, Quebec, Canada) at 100 µg/ml. Finally DNA was extracted with phenol and ethanol/sodium acetate precipitation before final precipitation with ethanol. The samples were analyzed on 1.0% agarose gel (ICN Biomedicals, Mississauga, Ontario) containing 50 µg/ml ethidium bromide. Electrophoresis was carried out in TE buffer (10 mM Tris-HCl, 1 mM EDTA at pH 8.0) for 18 h at 20 V.

Immunofluorescence microscopy. For indirect immunofluorescence microscopy of cultured cells, the fibroblasts of predetermined growth properties were cultured on glass coverslips. All the fibroblasts were fixed in 50% methanol:50% acetone for 10 min at −20° C. After air drying, the cells were rehydrated in PBS at pH 7.2 and incubated with the anti-terminin mouse monoclonal antibody (Mab 1.2) overnight at room temperature. The specimens were washed three times with PBS and incubated for 30 min with rabbit anti-mouse immunoglobulin G+immunoglobulin M (IgG+IgM) immunoglobulins (ICN Biomedicals) at room temperature. The samples were rinsed three times with PBS and incubated with fluorescein-conjugated goat anti-rabbit IgG (ICN Biomedicals) and incubated as before. The cells were finally washed with PBS and mounted in glycerol-containing PBS for epi-illumination examination of immunoreactive samples with a Nikon Labophot microscope.

Cell solubilization, SDS-PAGE, and immunoblotting. All the manipulations were done at 4° C. Fibroblasts ($3 \times 10^6$ cells) were washed with PBS and lysed in 1 ml of RIPA buffer (10 mM Tris-HCl, 150 mM NaCl, 1% Triton X-100, 0.1% SDS, 1 mM EDTA at pH 7.4) containing 0.5 mM phenylmethylsulfonyl fluoride (PMSF) (Sigma Chemicals, St. Louis, Mo.), 10 µg/ml aprotinin (Boehringer Mannheim), 2 µg/ml each of pepstatin and leupeptin (Boehringer Mannheim) and subsequently scraped and incubated for 10 min on ice. The samples were washed at 15,000 g at 4° C., and the detergent-insoluble fraction was washed once with 10 mM Tris-HCl, pH 7.4. The pellet was digested with 0.1 mg/ml of DNAse I (Sigma Chemicals) in a Tris buffer containing 10 mM Tris-HCl, 150 mM NaCl, 5 mM MgCl$_2$ at pH 7.4 supplemented with PMSP and aprotinin at 4° C. for 2 h with constant mixing. The sample was centrifuged for 10 min and further washed once with 10 mM Tris-HCl, 10 mM NaCl at pH 7.4 and a second time with Tris buffer only. The insoluble fraction was suspended in 10 mM Tris-HCl, 100 mM NaCl, 0.4% SDS at pH 7.4 containing PMSF, aprotinin, leupeptin, and pepstatin as mentioned above, sonicated briefly, boiled for 10 minutes, and analyzed on SDS-PAGE as described by Laemmli in Nature 227:680–685 (1970). After transfer to nitrocellulose paper as described by Laemmli, the blots were incubated with anti-terminin mouse monoclonal antibody (Mab 1.2), and the rabbit anti-mouse IgG (whole molecule) (Cappel Organon Teknika N.V., Turnhout, Belgium) was used as second antibody and peroxidase-conjugated goat anti-rabbit IgG (whole molecule) (Cappel) as the tertiary antibody with 4-chloro-1-naphtol (Sigma Chemicals) and $H_2O_2$ as peroxidase substrate. Nonspecific immunoreactive bands were identified by incubation with control ascites generated from a mouse myeloma cell line (PAI) which secretes no specific antigenic activity.

RESULTS

Induction of Cell Death during Serum Deprivation

Figure 1A:
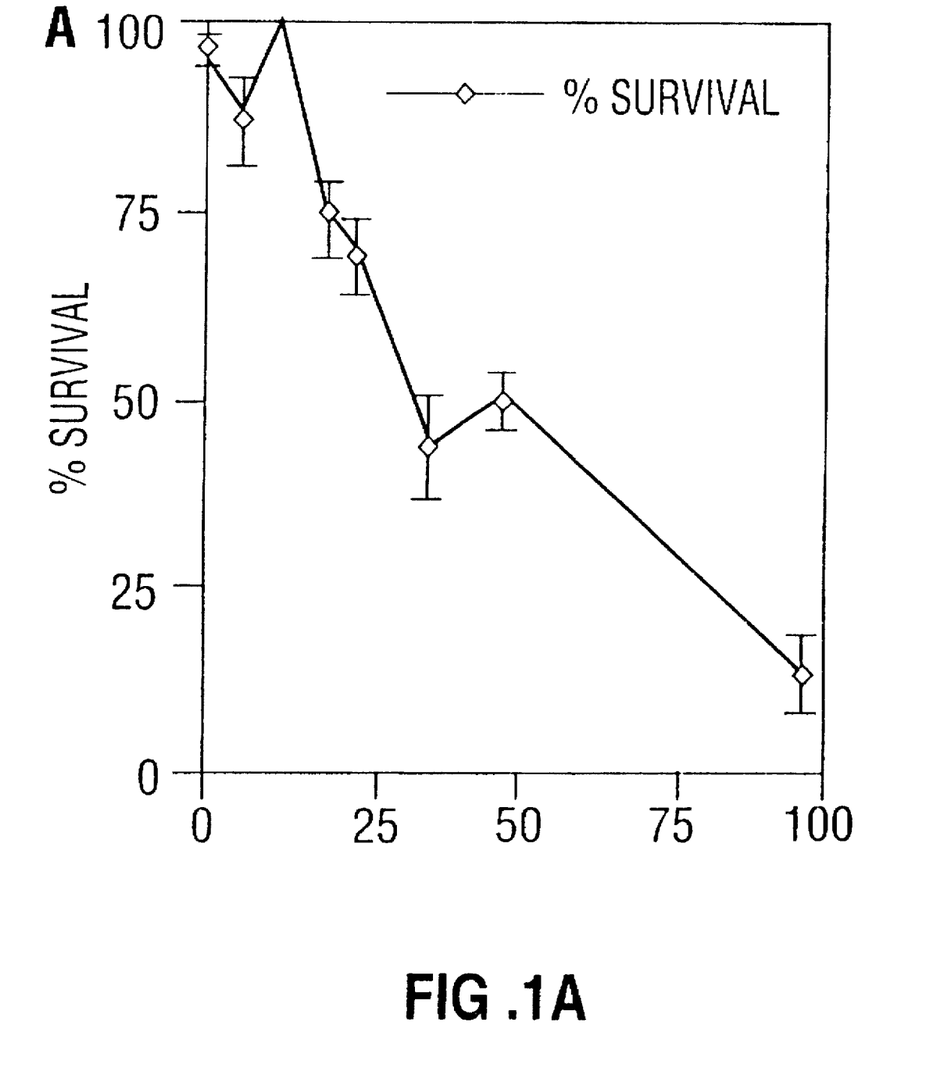

Factor withdrawal is known to induce apoptosis in many systems. To examine the expression of terminin during the induction of cell death, the inventor chose to study mouse 3T3 fibroblasts which were maintained under three different culturing states: proliferating (log phase), serum-deprived, and "revived" cells. The cell viability during such treatments was ascertained by the trypan blue dye staining method. To optimally synchronize growth status, all cultures were initiated from completely quiescent cells, accomplished by leaving confluent monolayers ($3 \times 10^4$ cells/cm$^2$) in 10% serum for 24 to 48 h. After passing the cultures of a lower cell density ($1.5 \times 10^4$ cells/cm$^2$) to media containing either 10 or 0% serum, subconfluent cells cultured in 10% serum (control) were shown to grow exponentially by [$^3$H] thymidine incorporation. In contrast, the proliferative capacity was lost in cultures in medium with 0% serum. FIG. 1A shows the effect of serum deprivation on the survival kinetics of 3T3 cells. After a period of 12 h where relatively few cells were dying, there was a gradual loss of viability up to 96 h.

Figure 1B:
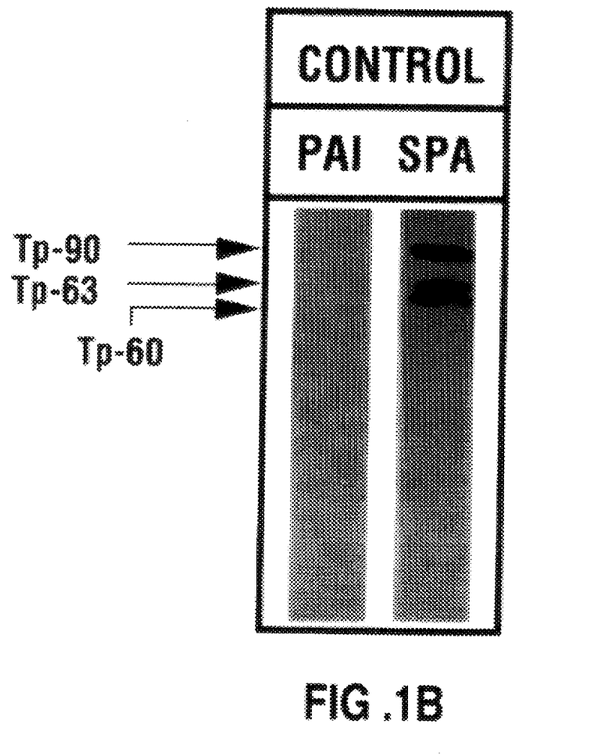
Figure 1C:
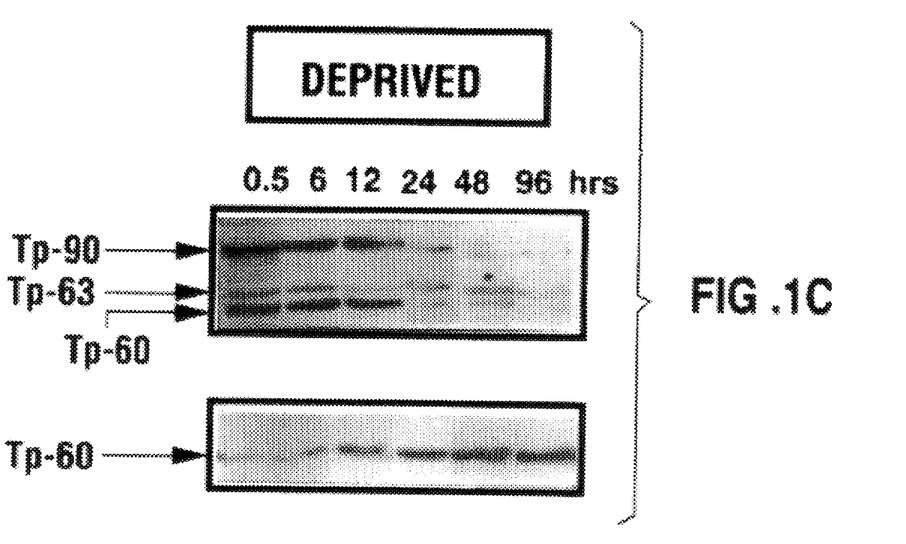

The Inventor further analyzed terminin expression in cells at various stages of these physiological states by immunoblotting. Control proliferating cells contained terminin in three forms with different relative molecular masses: Tp90 (terminin protein, 90 kDa), Tp63 (terminin protein, 63 kDa), and Tp60 (terminin protein 60 kDa); most immunoreactive material was found in the slowest migrating band (Tp90) (FIG. 1B). No cross-reactive band could be observed in the control PAI incubation. After 24 h of serum deprivation, Tp90 was reduced, Tp60 was increased, and Tp63 was underrepresented in parallel with the appearance of a new band of immunoblot analysis with M, 30 kDa (Tp30). Tp30, which was already visible after 30 min of serum removal, became the principal polypeptide species, which increased in intensity in later time points, as observed in immunoblot analysis using the monoclonal antibody, up to 96 h (when most cells were dead) (FIG. 1C). To evaluate the possibility of general protein degradation during this specific process of induced cell death, we studied the expression of actin by immunoblot analysis and found that the actin was stable up to 24 h (data not shown).

Figure 2:
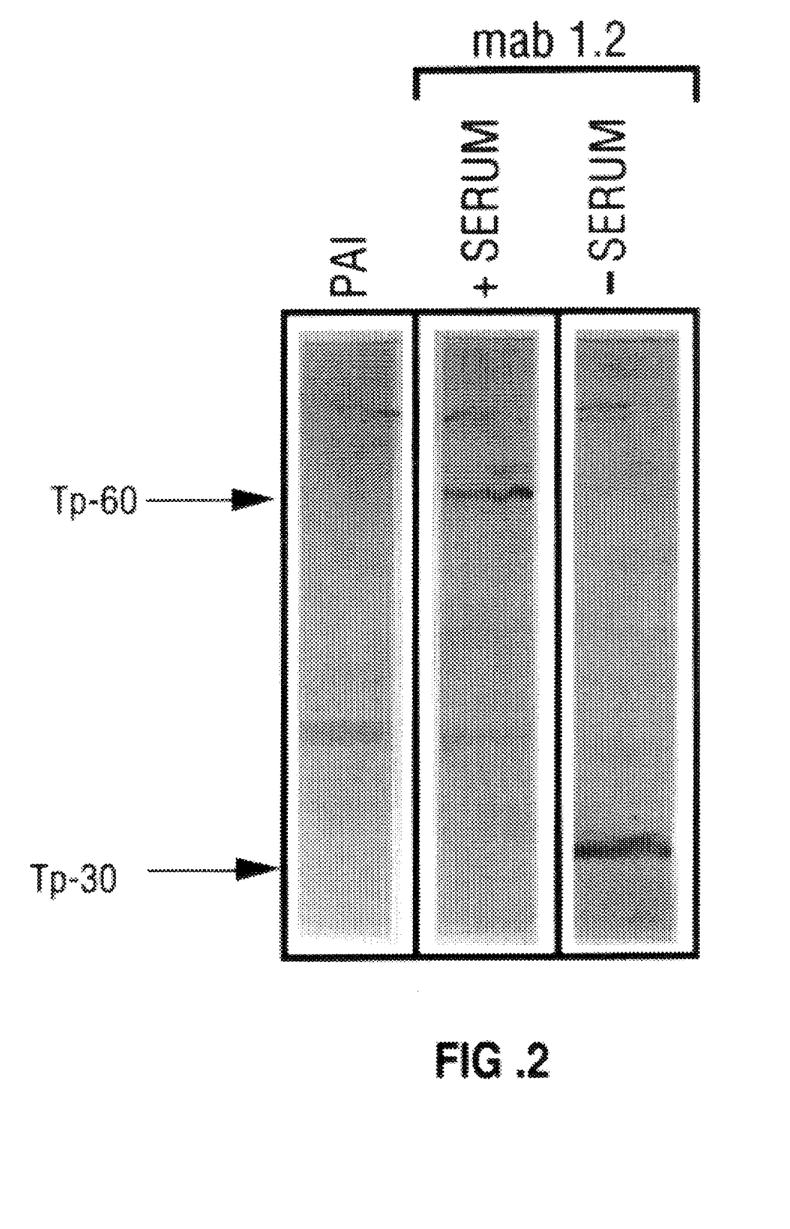

To verify if the same phenomenon of appearance of Tp30 during cell death could occur in other cell lines, we performed the same serum deprivation experiments with human diploid fibroblasts (GM3529; donor, 66 years old). Transfer of in vitro aged human cells to serum-depleted medium also lead to the appearance of Tp30 as the major protein after 28 days of such treatment (FIG. 2), as opposed to Tp90 and Tp60 expression in serum-containing young and senescent fibroblast cultures, respectively as described in Wang and Tomaszewski, J. Cell Physiol 147:514–522 (1991). Consequently, mouse 3T3 and human fibroblasts responded to serum removal and induction of cell death in a similar fashion, by generating Tp30, except the timing of its appearance takes longer for senescent fibroblasts.

Figure 3:
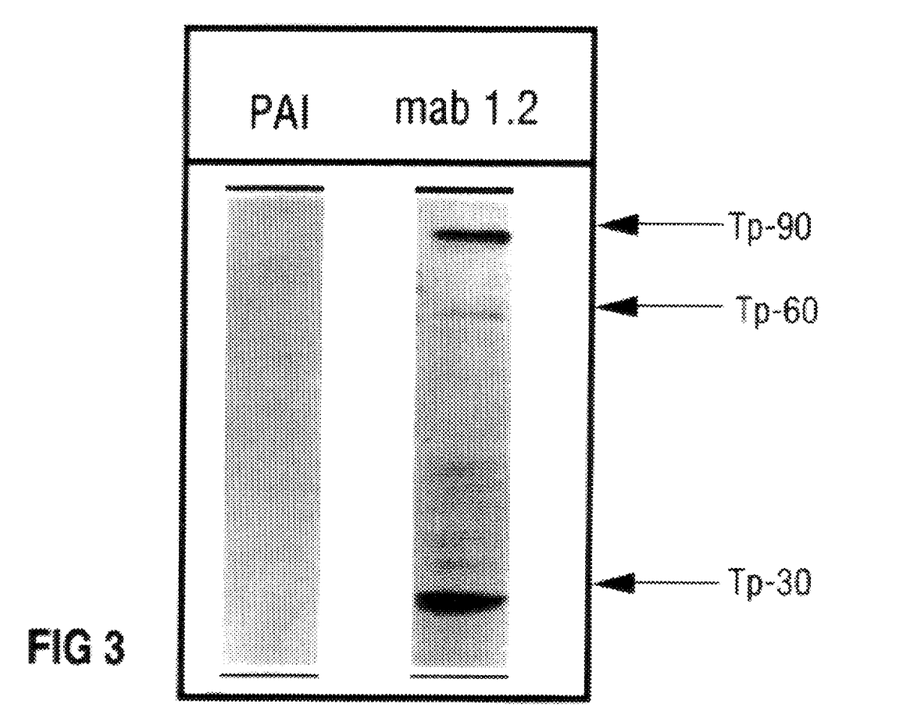

The inventor investigated whether the Tp30 was generated because of the specific proteolysis, which is activated due to the sparse density conditions of serum deprivation only, or during general cell death mechanism. To approach this, cell death was induced in the mouse 3T3 cells with the chemical agent cytosine β-D-arabinofuranoside (Ara-C) at 10 μM for 24 h which will kill any cell getting into DNA synthesis, and this killing effect occurs even in presence of 10% serum (Tamm et al. Proc. Natl. Acad. Sci. USA 88:3372–3376 (1991)). As shown in FIG. 3, the Tp30 immunoreactive band appeared by immunoblot in the Ara-C-treated dying population of cells, along with a weak band of Tp90 as opposed to the presence of Tp90/63/60 in the untreated cells as seen in FIG. 1B. These results established that the Tp30 appearance was specific to a death-related phenomenon.

Figure 4:
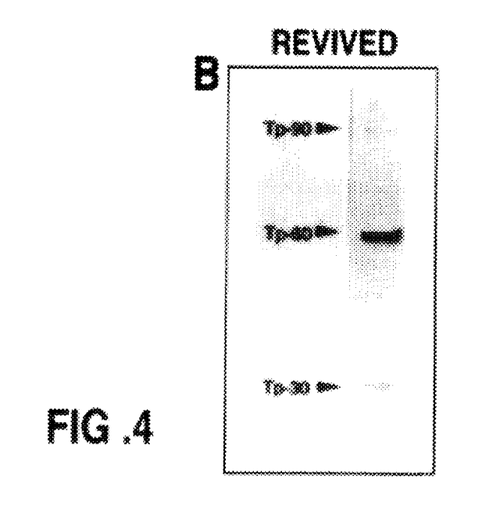

To further correlate the Tp30 presence and the activation of the death process by serum deprivation process, the 3T3 fibroblasts were revived with fresh serum at various times after serum removal. The ability to revive cells by adding 10% serum back to the culture can only be achieved up to 24 h of serum deprivation. Any time thereafter, for example, after 48 h of serum deprivation, revival cannot be done as demonstrated by the trypan blue exclusion assay. Survival kinetics during revival showed that cells could be revived with the maximum of 18 h of serum deprivation. Furthermore, upon immunoblot analysis, it was demonstrated that Tp60 became the major terminin species when cells that were deprived of serum for 12 h were revived with medium supplemented with 10% serum for 48 h (FIG. 4. This suggests that mouse 3T3 fibroblasts after 24 h of serum deprivation appear to be committed to the cell death mechanism and may have permanently lost the ability to be revived.

Figures 5A, 5B:
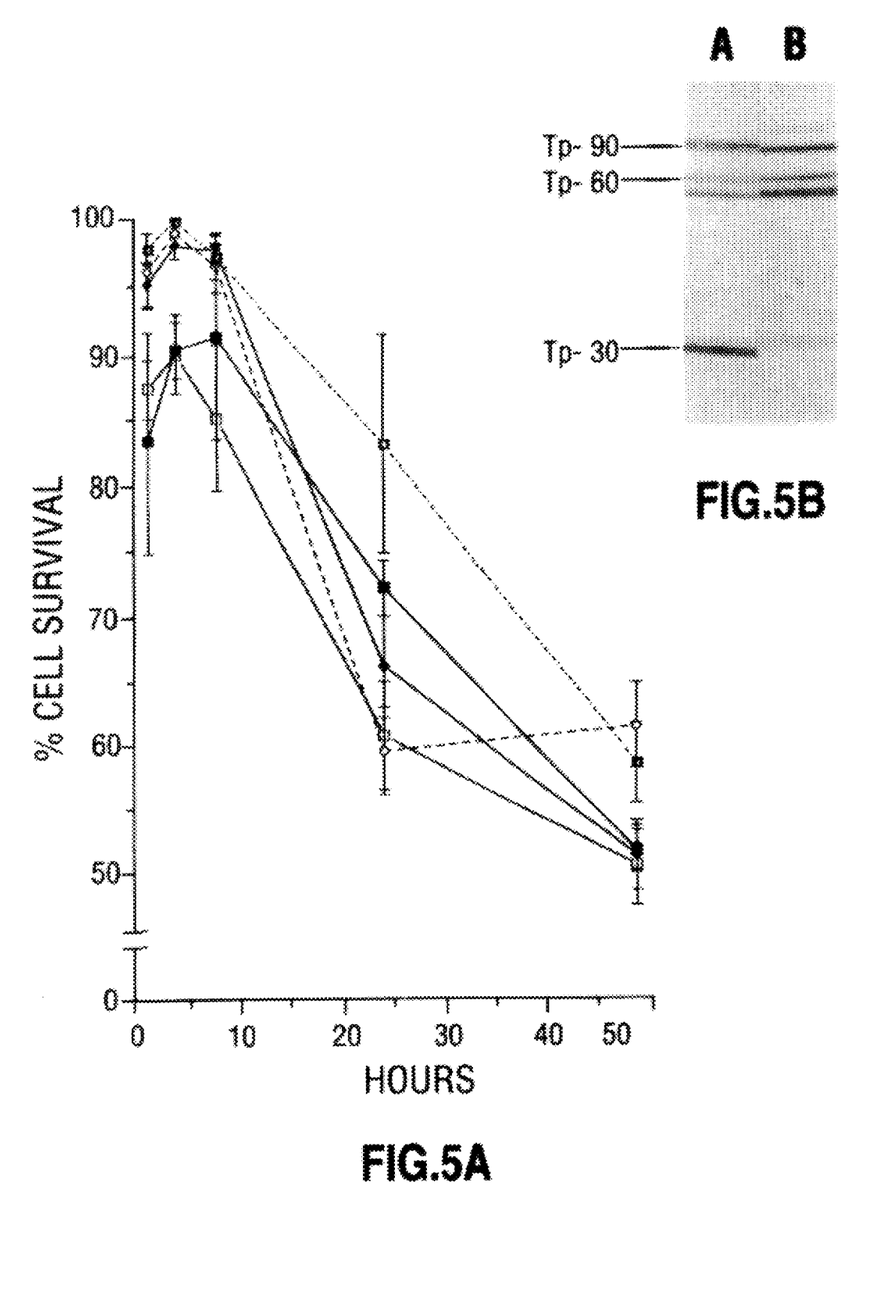

A striking feature of death induced by factor withdrawal is its highly modulated response by protein synthesis inhibitors such as cycloheximide (CHX); a decline in protein synthesis during apoptosis usually delays or inhibits cell death. Since Tp30 appearance seems to be an early event during induction of cell death by serum removal, the effect of CHX on the survival kinetics of Swiss 3T3 cells and Tp30 expression was investigated. CHX was added to control proliferating cells for 30 min (pretreatment) and then removed before serum deprivation. CHX was tested at concentrations of $10^{-3}$, $10^{-4}$, $10^{-5}$, and $10^{-6}$M. CHX ($10^{-4}$M) significantly increased (0.02<α<0.10) the proportion of cells remaining viable between 1.5 and 24 h of serum deprivation, compared to cells which were not pretreated with CHX but were serum deprived (control population) (FIG. 5A). Furthermore, CHX added to 3T3 cells during serum deprivation at Time 0 for 5 or 20 h became lethal to the cells (data not shown). In such circumstances, however, cells could be kept alive if serum was added with the CHX, confirming previous results (Fischback, G. D. (1972) Dev. Biol. 28:407–429). Pretreatment of confluent quiescent Swiss 3T3 cells with CHX ($10^{-5}$M) before serum deprivation results in the reduction in the amount of Tp30 protein produced, while the intensity of the other terminin subspecies was slightly stronger (FIG. 5B). This result suggests that the CHX pretreatment may reduce the potency of the putative proteolytic action, thus the amount Tp30 with the parallel observation of the reduction the dying cell number as shown in FIG. 5A. The mechanism of induced cell death would thus require active protein synthesis and modulation of Tp30 expression.

Figure 6A:
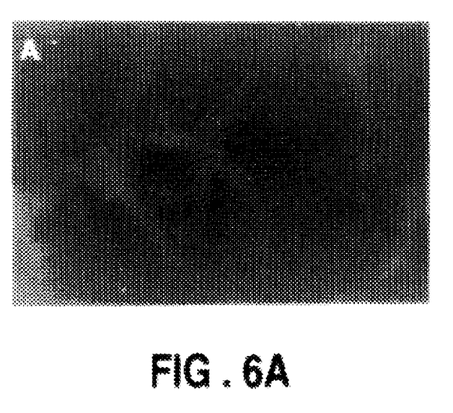
Figure 6B:
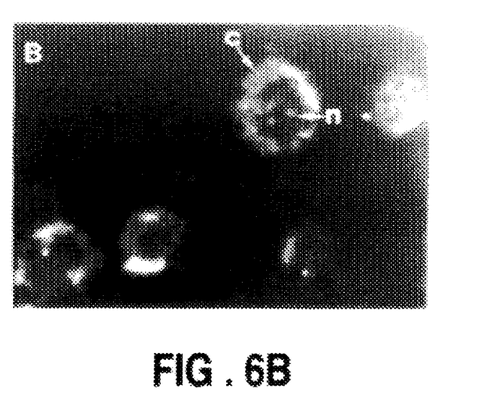
Figure 6C:
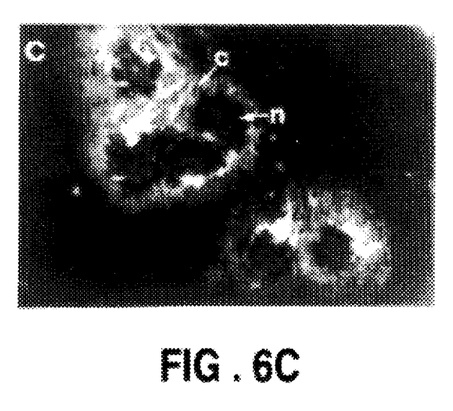
Figure 6D:
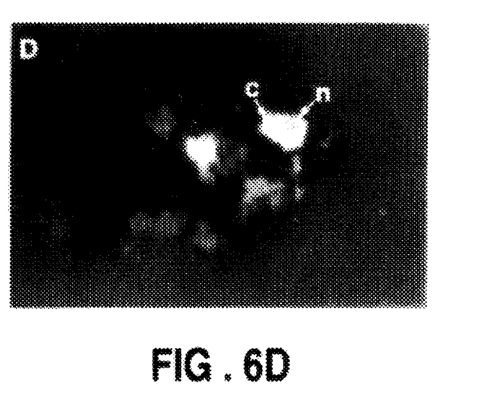

Immunofluorescence microscopy shows that terminin antibody staining activity is not detected in control proliferating cells (FIG. 6A). After 6 h in serum-free medium, antibody staining was detected predominantly in the cytoplasm, concentrated around the nucleus (FIG. 6B). By 24 h after serum deprivation, immunoreactivity appeared to be evenly distributed throughout the cytoplasm (FIG. 6C). None of the floating dead cells showed any reactivity to the antibody. After 96 h of serum removal, a condensed "granular" type of staining was observed in cells which appeared to have lost most of their cellular organization (FIG. 6D). The cytoplasmic staining present in the serum-deprived culture, specifically those cells which remained attached to the substratum, disappeared when fresh medium containing 10% serum was added in time during serum deprivation and as described in the legend to FIG. 4 (data not shown). The addition of nutrients during serum deprivation may thus abolish the induction of immunodetectable terminin in the revived cells.

Induction of DNA Fragmentation during Serum Deprivation

Figure 7:
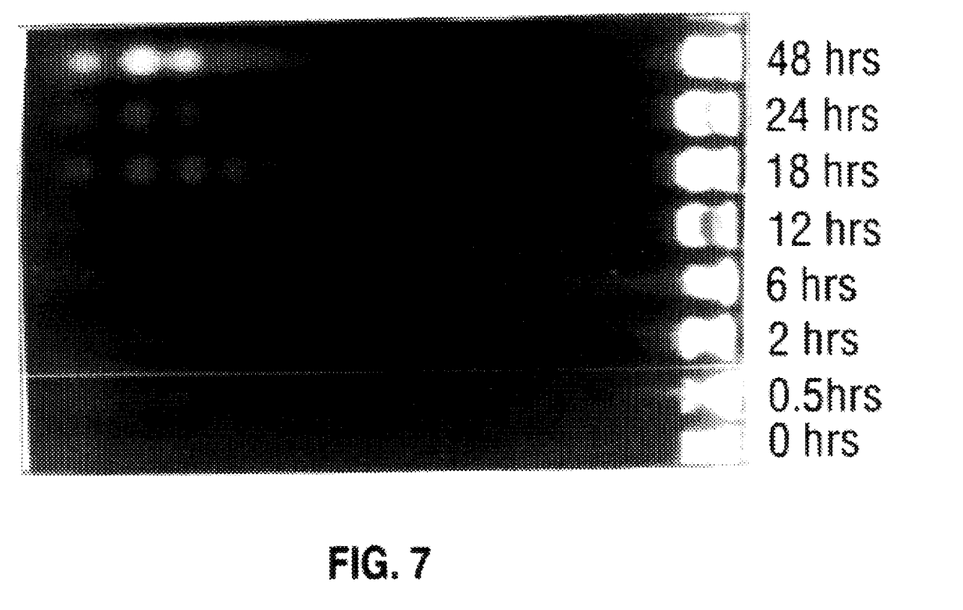

The inventor verified the nature of death mechanism induced in their system by serum deprivation by extracting DNA at the indicated time points (FIG. 7). No DNA degradation was visible when obtained from (1) proliferating cells in 10% serum and (2) 3T3 cells which sustained serum removal up to 8 h. As shown in FIG. 7, DNA degradation into oligonucleosomal-size fragments was observed by 12 h after serum deprivation of the confluent cultures (FIG. 7). DNA fragmentation to an oligonucleosomal ladder became clearly visible by 18 h of serum removal and increased with time up to 96 h. The same DNA ladder was observed when cells were killed by the Ara-C treatment as described in the legend to FIG. 3. CHX pretreatment ($10^{-4}$M) followed by serum deprivation for 24 h resulted in a visible reduction in the intensity of DNA fragmentation and the disappearance of the low-nucleosome-size fragments. These results suggest that CHX pretreatment can delay both the DNA fragmentation and the appearance of Tp30 in the serum-deprived Swiss 3T3 cells.

DISCUSSION

Understanding the mechanism of programmed cell death is currently the focus of many studies. Morphological features and DNA fragmentation into oligonucleosomal fragments are the only characteristic features of apoptosis in most of the systems studied so far. These features might be the result of the late events in the cascade leading to cell death. There would be several preceding (including proteolysis) events taking place before the DNA fragmentation and morphological changes.

The results presented above demonstrate the role of specific proteolysis of a known protein during the programmed cell death. Terminin was identified as a 90-kDa protein in young growing and nongrowing cells and in senescent human diploid fibroblast as a 60-kDa cytoplasmic protein. The anti-terminin monoclonal antibody 1.2 cross-reacted with a 90- and 60/63-kDa polypeptides in healthy 3T3 cells. Furthermore, the appearance of Tp30 as a result of specific proteolysis of Tp90 and Tp60/63 after serum withdrawal in mouse 3T3 fibroblasts can be used as a good cellular marker for indicating the initiation of cell death. Serum deprivation in this cell line activates apoptosis as shown by DNA fragmentation into oligonucleosomal-size fragmentation. The terminin protein of 30 kDa (Tp30) appears very early after serum deprivation, even before a noticeable degree of DNA fragmentation can be observed (18 h), and in parallel with immunohistochemical detection of terminin antibody staining within the cytoplasm of the cells. The results obtained with the induction of cell death by a chemical agent in the presence of serum further suggest that the process seen here resembles other apoptotic events such as glucocorticoid-induced cell death (Galili et al. (1984) Cancer Res. 44:4594–5601) and that Tp30 is indeed an early marker signalling this phenomenon, even before any events leading to final death occur.

When subjected to serum deprivation, senescent human fibroblasts were resistant to cell death and remained alive for several weeks after serum deprivation (inventor's unpublished results); the 60-kDa terminin species remains at the same level of quantity and the same molecular weight. However, when Swiss 3T3 cells were subjected to serum deprivation as described before, they underwent apoptotic cell death immediately and there was specific proteolytic degradation of Tp90, Tp60, and Tp63 into the 30-kDa form of the terminin polypeptide which increased with time. This result suggests that this kind of proteolysis might by playing an important role and is an early event in the process of cell death. The degradation of larger size terminin polypeptide into the 30-kDa form (Tp30), which is resistant to further degradation, might be due to either the activation of a specific protease or the accessibility or susceptibility of terminin polypeptides to a general protease action during the induction of apoptosis in 3T3 cells. Nevertheless this proteolytic action may play a significant role in programmed cell death and may be at the same time indirectly associated with the proteolysis of terminin polypeptides to the 30-kDa form.

Proteolysis of lamin B and topoisomerase I and II has been shown to occur during drug-induced apoptosis of myeloid (Kaufmann, S. H. (1989) Cancer Res. 49, 5870–5878) and mesenchymal cells (Ucker, D. S. Obernmiller, P. S. Eckhart, W., Apgar, J. R. Berger, N. A., and Meyers, J. (1992) Mol. Cell Biol 12, 3060–3069). It has been suggested that proteolytic events at nuclear membrane and matrix may precede internucleosomal cleavage of DNA by endonucleases (Oberhammer, FP., Wilson, J. W., Dive C., Morris I. D. Hickman, J. A., Wakeling, A. E. Waker P. R. and Sikorska, M. (1993) EMBO J. 12. 3679–3684). It has been observed that there is cleavage of DNA into 300- and/or 50-kDa fragments prior to actual internucleosomal fragmentation (Wyllie, A. H. (1992) Cancer Metastasis Rev. 11 95–103). The results suggest that the specific proteolysis of terminin, which is a cytoplasmic protein, is an earlier cellular event which occurs before the massive DNA fragmentation.

It is well established by now that factor withdrawal induces cell suicide as demonstrated with neuronal cells requiring nerve growth factor to survive (Martin, D. P. Schmidt, R. E. DiStefano, P. S. Lowry, O. H., Carter, J. G., and Johnson, E. M.,Jr. (1988) J. Cell Biol 106, 829–844) and lymphocytes depending on a specific lymphokine to live (Kyprianou, N. and Isaacs, J. t. (1988) Endrocrinology 122:552–562). The death process can be prevented by interference with macromolecular synthesis (Landon, C., Nowicki, M., Sugawara S., and Dennert, G. (1990) Cell Immunol. 128, 412–426). Apoptosis in the fibroblast system studied here required protein synthesis since the process was delayed by pretreatment of the cells with CHX as observed with MCF-7 breast cancer cells under the same conditions (Geier, A., Beery R., Haimshon, M., Hemi, R., and Lunenfeld, B. (1992) Cell. Dev. Biol. 28A, 415–418). Such a delay of the death process is also suggestive that necrosis is not being studied since it was shown that the latter is increased by CHX in various tissues (Martin, D. P. Schmidt, R. E. DiStefano, P. S. Lowry, O. H., Carter, J. G., and Johnson, E. M.,Jr. (1988) J. Cell Biol 106, 829–844). CHX treatment also caused decrease in the proteolysis of Tp90 and Tp60 as shown by the reduction in the amount of Tp30 expression. Meanwhile, the intensity of the Tp90/63/60 proteins became darker. The correlation between the reduction of Tp30 and the rescue from death by CHX treatment further suggests that the presence of Tp30 is a result of specific proteolysis of terminin as an apoptosis-dependent event.

The revival experiments with fresh serum demonstrated the time-dependent fashion for the final death event occurring during apoptosis. A population of mouse 3T3 fibroblasts could reenter the traverse of the cell cycle after 24 h at maximum serum deprivation if and when they are supplied with serum again. These results confirmed that the process leading to the final death was reversible up to a certain "commitment" as previously reported by Dowd D. R. and Meisfeld Dowd, D. R., and Miesfeld, R. L. (1992) Mol. Cell. Biol. 12, 3600–3608. It is well established that mouse 3T3 cells can be revived after serum deprivation (Zetterberg, A., and Larsson, O. (1985) Proc. Natl. Acad. Sci. USA 82, 5365–5369). This was exemplified with another cell line, rat fibroblasts, which during factor removal could escape the first wave of apoptosis and start DNA synthetic activity at about 12 h of serum deprivation (Evan G. I. et al. 1992. Cell 69:119–128). In the present study, the possibility of going through the cell cycle traverse once again by cells that have been serum deprived for 24 h is probably due to a residual subpopulation of fibroblasts which still express, between 24 to 48 h of serum withdrawal, the Tp90, Tp63, and/or Tp60 proteins and are not far ahead into the apoptotic process. The immuno-refractoriness to do so after 24 h of serum removal could well be correlated with the extensive DNA fragmentation which occurs thereof and which could be part of the commitment step to cell death.

Tp30 remains an early marker for commitment of cell death and supports the hypothesis that Tp30 is implicated in a specific death-related signalling cascade. Indeed, the importance of Tp-30 during cell death is signified by (1) its increasing amount with time up to 48 h during serum deprivation and treatment with cell-killing agents; (2) its decreased concentration in cells pretreated with cycloheximide undergoing delayed apoptosis; and (3) its decreased amount in cells rescued from death by adding serum back to the culture. Furthermore, a high level of DNA fragmentation occurs already at 24 h at which time point Tp30 expression is at its maximum. These results suggest that the apoptotic and not necrotic event in mouse 3T3 cells during serum withdrawal is being examined.

B. APPLICATIONS OF INVENTION

With the knowledge that Tp30 can be used as a marker for cell death commitment, many practical applications for the Tp30 protein, the Tp30 nucleic acid sequence and antibodies to Tp30 can be realized.

For example, the monoclonal antibody (Mab 1.2) can be used to detect cell death status in several situations as follows:

1. routine pathological diagnostic tests of solid tissues;
2. fluorocytometric studies of peripheral lymphocytes;
3. assessment of the effectiveness of chemotherapeutic drugs; and
4. assessment of the effectiveness, by the consequential impact on cell death status, of gene therapy.

The following sections describe some of the ways in which the presently available monoclonal antibody (Mab 1.2) can be used in the detection of cell death status.

1. Routine pathological evaluation of cell death status of solid tissues

This assay can be performed first by immunohistochemical assays in combination with immunoblotting assays. Biopsy tissues are separated into two portions. One portion is processed by formaldehyde-fixation or rapid freezing for frozen sectioning; 6–10 micron sections are incubated with either the Mab 1.2 hybridoma culture supernatant or the ascites form. After incubation overnight at room temperature, these specimens are further incubated with secondary antibody conjugated with fluorescein isothiocyanate for immunofluorescence microscopy, or with horseradish peroxidase for immunoperoxidase examination. The completed processed samples can then be examined for cytoplasmic staining activity by positive reaction. After evaluation by microscopic examination that a positive reaction is present, the second portion of the biopsy tissue is then processed for extraction of the detergent-insoluble fraction, which is then processed for SDS-PAGE electrophoresis to separate the different protein species in the extract, followed by transferring to nitrocellulose (NC) paper and reaction with Mab 1.2. The detection of Tp30 presence is accomplished by hybridizing Mab 1.2 with the NC paper, followed by a revealing reaction with secondary antibody conjugated with horseradish peroxidase. The cell death status can be determined by the qualitative and quantitative presence of a Tp30 band, as well as the positive staining reaction with Mab 1.2.

At present, cell death status can be evaluated based on DNA integrity. The popular assays for this determination are either the biochemical assaying DNA on agarose gel for DNA breaking into oligonucleosome ladders, or immunohistochemically assaying the nicked end of DNA by labelling the free DNA end with fluorescein or horseradish peroxidase-conjugated UTP via terminal transferase. Routinely, one can also examine nuclear morphology by propidium iodide (PI) staining. All three assays (DNA ladder, end-labelling, and PI labelling) are gross measurements and only good for those cells that are already dead or at the end stage of dying. Compared with these three assays, the present invention using the monoclonal antibody to Tp30 is superior, since it detects not only those cells that are dead but also those cells that are committed to die. Therefore, it provides a broader picture of death status with a quantitative estimation of Tp30 presence.

2. Fluorocytometric studies of cell death status with peripheral lymphocytes

The present technology of fluorocytometric studies employs the identification of cells at three different phases of the cell cycle: $G_1$, S, and $G_2$. This is largely performed by DNA quantity staining by propidium iodide labelling. Since the dying cell population contains the same DNA quantity as the living counterparts at any of the three phases of the cell cycle, there is no way to distinguish the two cell populations. The present invention allows one to perform double labelling for terminin (Tp30) positivity and propidium iodide (PI) staining together. Measurement of the labelling indices for Tp30 and PI staining can be used in combination to obtain the exact fractions of those cells in $G_1$ that are living (Tp30-positive) and dying (Tp30-positive). Similar estimation can be made for the S-phase and $G_2$ phase cell populations.

Peripheral lymphocytes may be obtained according to the standard procedure through Ficoll gradient separation, and then processed for formaldehyde fixation and extraction with 0.05% Triton. Afterwards, the cell specimens are incubated with monoclonal antibody (Mab 1.2) to Tp30 overnight at room temperature or at 37° C. for one hour. This is followed by further incubation with fluoresceinated goat antimouse antibody, and subsequent incubation by propidium iodide staining. The completely processed cell specimens are then evaluated by fluorocytometric measurement on both fluorescence (Tp30) and rhodamine (PI) labelling intensity on a per cell basis, with the same cell population simultaneously.

3. Assessment of inhibitory effect on cell growth by chemotherapeutic induction of programmed cell death So far, the routine method to determine whether a particular chemotherapeutic drug can inhibit cancerous cell growth is to examine cell population size either in culture, by measuring the reduction in cell colony size or number, or measuring soft agar colony growth or in vivo tumor formation in nude mice. All three procedures require time for development of the colonies or tumor to be large enough to be detectable. Experiments involved in these approaches in general require large-scale planning and multiple repeats of lengthy experimental span (at least three weeks). Often these assays do not take into account the fact that a drug may not be inhibiting cell growth, but rather killing the cells; this type of effect may be a more favorable consequence needed for chemotherapeutic treatment of cancer. Previously the inventor isolated a 57 kDa protein, termed statin, that is specific for quiescent, non-cycling or non-proliferating cells. (Mitmaker et al., Eur.J.Histochem. 37:295–301, 1993). The inventor also has developed a monoclonal antibody S-44 that is specific for statin. Statin and the monoclonal antibody S-44 are useful in assessing the non-proliferating population of cells in a given tissue which indirectly gives a measure of the proliferating component of a tumor or cell mass. The combination of using statin antibodies to detect the nonproliferating cell population pool, and terminin antibodies to detect the dying cell population pool, provides a powerful and rapid assessment of the effectiveness of any given drugs in the containment of cancerous cell growth. Specifically, the antibody to statin allows evaluation of whether the drug treatment inhibits the cancerous cells from further growth (statin is absent in both proliferating and dying cells), and the antibody to terminin Tp30 provides the means to study whether, and to what extent, the drug treatment kills the cells. Application can be easily performed at the immunofluorescence microscopic level with cultured cells or tissue sections, and the results can be obtained both qualitatively and quantitatively in a week. All together, these approaches can avoid the time-consuming and manpower-demanding assays such as colony formation, soft agar, or tumor production determinations.

4. Assessment of pharmacological intervention on inhibition of cell death frequency in degenerative diseases In contrast to neoplasia, where the disease develops due to too many cells growing, many clinical symptoms are derived from losing functional units through too many cells dying. For degenerative diseases such as Alzheimer's or Parkinson's disease, these losses may be due to the premature activation of the cell death program in neurons. In osteoporosis, the cell loss may be due to an improper balance between osteoblast and osteoclast cells, due to the too active programmed cell death process killing more cells than the bone tissue can afford. Other related phenomena may also occur in the wound healing process, tissue transplantation and cell growth in the glomerus during kidney infection, where the balance between living and dying cell populations is an essential issue to the health status of the tissue. The present invention provides a rapid assessment of dying cell populations through the immunohistochemical and biochemical measurements of Tp30 presence in degenerative tissues.

5. Assessment of cell death in tissue due to infection by bacteria and HIV and other classes of viruses that can induce cytopathic effects In general, many viral infections are accompanied by the final disintegration of the infected cells. Traditionally, the precipitous effect of these viral infections is the activation of programmed cell death, therefore allowing the cells to contain the scope of infection in a given tissue. However, if this suicide is too active to be stopped at the right level, tissues will lose too many cells during the course of infection, therefore resulting in an adverse effect and ultimately a disease situation. One of the most noted examples is the activation of CD4 T-cells to kill other cell types, in HIV infection. The present invention using the monoclonal antibody to Tp30 allows us to measure cell death status in terms of frequency and dying cell population in bacterially- and virally-infected tissues. Measurements of cell death status can be performed by the immunohistochemical and immunoblotting techniques described above and in Hubert, Pandey and Wang (1994). Similarly, the present invention can also determine the effectiveness of any treatment regimens in terms of reduction or suppression of cell death frequency and scope.

6. Assessment of cell death status in oligodendrocytes associated with Multiple Sclerosis Positive staining of monoclonal antibody to terminin Tp30 occurs in dying cultured human oligodendrocytes. The programmed cell death event is activated in these oligodendrocytes by total deprivation of serum, or by treatment with tumor necrosis factor (TNF). The inventor is examining whether the promiscuous killing of oligodendryocytes by CD4 cells is also associated with the appearance of Tp30. If so, the inventor may be able to explain whether the loss of oligodendrocytes associated with multiple sclerosis (MS) is due to the induction of programmed cell death by the CD4 cells, which come in contact with the oligodendrocytes when the blood-brain barrier deteriorates. Therefore, the present invention can be used in cultured oligodendrocytes to ascertain how drug intervention can deter the programmed cell death event in terms of frequency and scope in this cell system. In this context, the invention could help discover a drug which reduces the oligodendrocyte loss associated with the MS syndrome.

7. Assessment of cell death status in archival pathological tissue specimens that have been processed by the routine procedure of formalin-fixation and paraffin-embedding Normally, biopsy or autopsy samples processed in most clinical pathology laboratories are prepared in a harsh way of formalin fixation and paraffin embedding. While this is an accepted procedure for preservation of tissue morphology, fit for long-term storage and repeated examination, it destroys the antigenic activity necessary for studies by most antibodies, thus it becomes necessary to prepare frozen sections from tissue block that have been spared the above procedure, instead using the flash-freezing technique. Although most hospital pathology laboratories have adapted to this requirement, it is still not a routine procedure, and only selected samples are processed for frozen sections. It is apparent that if an antibody can stain both frozen and formalin/paraffin-prepared samples it will have a significantly broadened scope of application. Recently, we have found that the antibody to terminin (Mab 1.2) fits the criterion. In particular, it provides positive staining reaction in archival pathological samples of breast cancer tissues.

8. Assessment of cell death status in pharmacological studies in animal models

Attempting to control either a reduced cell death rate, in the case of cancer, or an increased cell death rate, in the case of neurodegeneration, has been recently seen as a new mode of disease intervention. Numerous approaches via either intervention with known drugs or gene therapy are in progress, starting from the base of correcting the altered programmed cell death process, with the concept on maintaining a balanced cell mass in any given tissue. For these therapeutic interventions, the bridge between studies in cultured cells and clinical trials is animal studies, i.e. success in intervention with animal models, in either routine laboratory animals or transgenic mice bearing either knock-out or overexpression phenotypes. Terminin antibody (Mab 1.2) is a powerful tool for examining apoptotic death status in terms of change in dying cell numbers between normal and experimentally manipulated animals. In this context the invention, as a diagnostic tool for assessing cell death status, could help to determine the efficacy and potency of a drug or a gene therapeutic approach.

The embodiments of the invention in which an exclusive property or privilege is claimed are difined as follows:

1. A terminin apoptosis protein having a molecular weight of about 30 kDa.

2. The protein according to claim 1 wherein said protein is Tp30.

3. A method of detecting disorders in which the natural regulation of cell death is interrupted comprising assaying a sample for the protein of claim 1.

4. The method according to claim 3 wherein said disorder is selected from the group consisting of cancer, bone degeneration, autoimmune diseases, neurodegenerative diseases, cardiovascular disorders, ischemia, HIV-associated illness, and kidney malfunction.

5. A method for diagnosing a disorder in which the natural regulation of cell death is interrupted comprising assaying a sample for the protein of claim 1 and correlating the presence or amount of the protein with diagnostic criteria for said disorder.

6. A method of determining the scope and frequency of programmed cell death in a tissue comprising measuring the amount of the protein of claim 1 in said tissue, measuring the amount of TP90 in said tissue, and comparing the amount of the protein of claim 1 to the amount of TP90 in said tissue.

7. The method according to claim 3 wherein the sample is selected from the group consisting of solid tissues and peripheral lymphocytes.

8. The method of claim 3 in which the protein is in labeled form.

9. The method of claim 5 in which the protein is in labeled form.

* * * * *